(12) United States Patent
Bentley

(10) Patent No.: US 7,611,732 B2
(45) Date of Patent: Nov. 3, 2009

(54) NUTRITIONAL SUPPLEMENT FOR OSTEOARTHRITIS

(76) Inventor: Michael Bentley, 1501 West Broadway Suite 400, Vancouver, BC (CA) V6J 4K9

(*) Notice: Subject to any disclaimer, the term of this patent is extended or adjusted under 35 U.S.C. 154(b) by 677 days.

(21) Appl. No.: 10/898,215

(22) Filed: Jul. 26, 2004

(65) Prior Publication Data
US 2006/0018976 A1 Jan. 26, 2006

(51) Int. Cl.
*A61K 33/12* (2006.01)
(52) U.S. Cl. .................. 424/602; 424/611; 424/682; 424/683; 424/684; 424/724; 426/73; 514/165
(58) Field of Classification Search ............... 424/602, 424/611, 682, 683, 684, 724; 426/73; 514/165
See application file for complete search history.

(56) References Cited

U.S. PATENT DOCUMENTS

| | | | | |
|---|---|---|---|---|
| 1,674,353 | A | | 6/1928 | Brackett |
| 2,531,439 | A | * | 11/1950 | Jordan .................. 426/72 |
| 3,658,984 | A | | 4/1972 | Kamp |
| 4,387,093 | A | | 6/1983 | Lysaght |
| 4,758,429 | A | | 7/1988 | Gordon |
| 4,810,496 | A | | 3/1989 | Jensen |
| 4,847,085 | A | | 7/1989 | Laurent |
| 4,968,510 | A | | 11/1990 | Jensen |
| 4,970,080 | A | | 11/1990 | Laurent |
| 5,035,888 | A | * | 7/1991 | Hara ................. 424/725.1 |
| 5,043,168 | A | | 8/1991 | Patel |
| 5,082,662 | A | | 1/1992 | Laurent |
| 5,252,345 | A | | 10/1993 | Hu |
| 5,879,698 | A | | 3/1999 | Ellenbogen |
| 5,895,665 | A | | 4/1999 | Irastorza |
| 6,303,572 | B1 | | 10/2001 | Rowe |
| 6,383,282 | B1 | * | 5/2002 | Chaiko ................. 106/486 |
| 6,468,964 | B1 | | 10/2002 | Rowe |
| 6,582,709 | B1 | | 6/2003 | Maor |
| 6,797,286 | B2 | | 9/2004 | Bobrowski |
| 7,135,198 | B2 | * | 11/2006 | Frater-Schroder et al. ... 424/725 |
| 2002/0172722 | A1 | | 11/2002 | Fanelli |
| 2003/0035844 | A1 | | 2/2003 | Samelson |
| 2003/0219493 | A1 | | 11/2003 | Samelson |
| 2004/0052871 | A1 | * | 3/2004 | Schakel et al. ............. 424/725 |
| 2004/0068130 | A1 | | 4/2004 | Bobrowski |

FOREIGN PATENT DOCUMENTS

JP 360241857 A * 11/1985
JP 409087687 A * 3/1997

OTHER PUBLICATIONS

Phillipson, J. New Drugs From Nature—It Could Be Yew; Phytotherapy Research 13 (1999) pp. 2-8.*

Revilla et al. Comparison of Several Procedures Used for the Extraction of Anthocynains From Red Grapes; J. Agric. Food Chem. 1998, 46, pp. 4592-4597.*

Merck Manual: Osteoarthritis; URL<http://www.merck.com/mmhe/sec05/ch066/ch066a.html?qt=osteoarthritis&alt=sh> pp. 1-4, accessed Nov. 22, 2006.*

Karayigit et al. Mineral Matter and Trace Elements in Miocene Coals of the Tuncbilek-Domanic Basin, Kutahya, Turkey; Energy Sources; 25 (2003), pp. 339-355.*

Preda et al. Temporal Variations of Mineral Character of Acid-Producing Pyritic Coastal Sediments, Southeast Queensland, Austrailia; Science of the Total Environment 326 (2004) pp. 257-269.*

Murray, M: Quercetin: Nature's Antihistamine; Better Nutrition; Atlanta, Apr. 1998, vol. 60, Issue 4, p. 10, pp. 1-4 of ProQuest.* mindat.org Smectite Group; mindat.org [online] URL<http://www.mindat.org/min-11119.html> one page, accessed Jul. 18, 2007.*

Miller et al. : Suppression of Human Cartilage Degradation and Chondrocyte Activation by a Unique Mineral Supplement (SierraSilTM) and a Cat's Claw Extract, Vincaria ® ; The Journal of the american Nutraceutical Association; vol. 7, No. 2, Spring 2004, pp. 32-39.*

Nutraceuticals World; Joint Health Supplement; Apr. 2004, vol. 7, No. 4 p. 56, one page of Promt print-out.*

Heritage Health Products; Cat's Claw; [online] URL <http://web.archive.org/web/20030216033456/www.heritagehealthproducts.net/catsclaw.html> pp. 103, accessed Jul. 18, 2007.*

Heritage Health Products; Cat's Claw; [online] URL <www.heritagehealthproducts.net/catsclaw.htm> pp. 1-3, accessed Jul. 18, 2007.*

Sierrasil.com: Sierrasil; [online] URL <www.sierrasil.com/about_ingredients.php> pp. 1-2, accessed Jul. 18, 2007.*

Kriegel Marketing Group: Sierrasil: Clinical Trial with the Mineral Compound Sierrasil to Determine Any Benefits to Osteoarthritis Patients; Press release, Mar. 3, 2004.*

Piscoya, et al., Efficacy and safety of freeze-dried cat's claw in osteoarhritis of the knee: mechanisms of action of the species . . . Inflammation Research, 2001, 442-448.

Miller, et al., Suppression of Human Cartilage Degradation and Chondrocyte Activation by a Unique Mineral Supplement.

Nutrazon Liquid Dietary Supplements, www.nutrazon-info.com/nutrazon_vincaria,html.

Trademark Registration No. 2,788,819, Vincaria, filed Sep. 29, 2002.

* cited by examiner

*Primary Examiner*—Patricia Leith
(74) *Attorney, Agent, or Firm*—Arlir M. Amado; Kramer & Amado, P.C.

(57) ABSTRACT

The present invention relates to a method of treating osteoarthritis by administering a mineral composition in the form of a nutritional supplement, where the mineral composition may contain Smectite, Gypsum, Quartz, Feldspar, Jarosite, Kaolinite and/or Zeolite.

10 Claims, No Drawings

NUTRITIONAL SUPPLEMENT FOR OSTEOARTHRITIS

BACKGROUND OF THE INVENTION

1. Field of the Invention

This invention relates generally to a nutritional supplement for the treatment of osteoarthritis. The nutritional supplement includes a purified mineral composition that may be administered to a subject suffering from osteoarthritis. The invention also relates to a method for treating osteoarthritis by administering a mineral composition.

2. Description of Related Art

Osteoarthritis is one of the most widespread forms of degenerative joint and bone diseases. The pathological condition is characterized by localized areas of loss of articular cartilage within the synovial joints, associated with hypertrophy of the bone and thickening of the joint capsule. The exact cause of osteoarthritis is unknown at this time, however the entire process is thought to involve a complex interaction of cells and soluble mediators such as cytokines, growth factors, inflammatory mediators, metalloproteinases, and chondrodegradative enzymes. This complex interaction may further be triggered by physical trauma, surgery, infection, or another disease process. In its more advanced stages, osteoarthritis is characterized by fraying and fibrillation of cartilage resulting from the elaboration of proteolytic and collagenolytic enzymes by the chondrocytes that initially attack the joint matrix. Inflammation of the synovial tissue develops and leads to an increase of cytokines that attack the cartilage. The synovitis also leads to an increase in edema, vascularity and severe pain in the joint.

The disease progression may range from relatively mild symptoms causing pain and swelling to extreme debilitation and physical incapacitation. Complete destruction of the cushioning tissue in the joints may also lead to bone erosion and required joint replacement. Osteoarthritis is a disease that affects all ages, but is more strongly pronounced among people 45 and older. At the present time over 4 million Canadians and 20 million Americans suffer from osteoarthritis; a number that will rapidly increase as the population continues to age. The high prevalence of this disease not only affects the individuals who suffer from it, but also presents increasing costs to the health-care industry and loss of productivity in the workplace.

Treatment regimens for osteoarthritis include exercise and stretching, over-the-counter medications and prescription drugs. Other pharmaceutical treatments have been proposed that directly mediate the cellular/inflammatory cytokine interaction that perpetuates the progression of the disease. While over-the-counter medications and prescription drugs are provided for symptomatic relief they cause a number of side effects that limit their usefulness to those suffering from osteoarthritis. For example, long-term use of high dosage non-steroidal anti-inflammatories such as aspirin, ibuprofen or acetaminophen may lead to upset stomachs, gastrointestinal bleeding and possible liver damage. Stronger prescription drugs such as corticosteroids may lead to brittle bones, cataracts and elevated blood sugar while disease-modifying anti-rheumatic drugs may suppress the immune system. Additionally, these treatment regimens may be both expensive and difficult to administer in the correct dosages and time intervals.

Nutritional supplements have also been used to bring about positive therapeutic effects in a number of ailments. Proteoglycan-based supplements such as chondroitin and glucosamine have become popular in recent years as sources of joint tissue precursors used to alleviate cartilage destruction cause by osteoarthritis. However, these supplements do not contain the inorganic minerals necessary for the overall treatment of osteoarthritis symptoms. Therefore there is a need for an inexpensive nutritional supplement that provides a composition of minerals for the treatment of osteoarthritis.

The foregoing advantages of the invention are illustrative of those that can be achieved by the present invention and are not intended to be exhaustive or limiting of the possible advantages which can be realized. Thus, these and other advantages of the invention will be apparent from the description herein or can be learned from practicing the invention, both as embodied herein or as modified in view of any variation which may be apparent to those skilled in the art. Accordingly, the present invention resides in the novel methods, arrangements, combinations and improvements herein shown and described.

SUMMARY OF THE INVENTION

In light of the present need for a nutritional supplement and method for treating osteoarthritis, a brief summary of the present invention is presented. Some simplifications and omissions may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention relates to a purified composition for the treatment of osteoarthritis. The composition may include Smectite, Gypsum, Quartz, Feldspar, Jarosite, Kaolinite and/or Zeolite. The composition may be administered to a subject suffering from osteoarthritis.

The present invention also relates to a method for the treatment of osteoarthritis. The method may include administering a composition to a subject suffering from osteoarthritis, where the composition contains Smectite, Gypsum, Quartz, Feldspar, Jarosite, Kaolinite and/or Zeolite.

DETAILED DESCRIPTION OF THE PREFERRED EMBODIMENTS OF THE INVENTION

The present invention includes a composition and method of treating osteoarthritis. The method may include administering a composition to a subject suffering from osteoarthritis, where the composition contains Smectite, Gypsum, Quartz, Feldspar, Jarosite, Kaolinite and/or Zeolite. The composition may be a purified form of sedimentary silt obtained from a river source, such as the Walker River in the Sierra Mountains of Nevada; however, the composition is not limited to this source. This combination of minerals has been shown to have positive effects when ingested by subjects suffering form osteoarthritis. However, each individual mineral may also produce positive effects based on its physical, chemical and therapeutic properties.

Smectite is a hydrous silicate of alumina that is composed of calcium, iron, magnesium and aluminum silicate. Smectite minerals are known for their absorbent and disintoxicating properties. The mineral has been used to treat peptic ulcers by alkanizing stomach acid and bacterial inflammation of the gastrointestinal tract. The crystalline network formed by the minerals composing smectite gives it unique surface conductivity that may lead to its therapeutic effects on inflammatory diseases. This conductivity may also apply to the other silicates found in this composition. Silicates tend to structurally arrange water molecules up to three layers (wetting). In the presence of molecular water, the silanol groups of small silicates ionize, producing mobile pro-tons that associate/dissociate with the surface to impart an electrical conductivity to the surface that attracts minerals and ions. These layers have been further described as the omega (o—innermost water layer), beta (b—second water layer) and delta (d—outermost water layer). The resulting surface-solution interface that exists at wetted mineral surfaces is called the electrical double layer or zeta potential. It is this characteristic that tends to transport small ions, minerals and electrolytes (i.e. hydrogen, iron, magnesium, calcium, and sodium, etc.). These SiOH groups and the resulting water arrangements tend to cage or sieve minerals. They also hold hydrogen atoms within these structures. When hydrogen is further reduced, a biological antioxidant property is maintained in the silicate mineral particle. Some nutritional investigators speculate that a silica mineral deficiency is involved in the causation of several human disorders including atherosclerosis, osteoarthritis and hypertension, as well as, the aging process Gyspum is a colorless, white or yellowish mineral composed of CaSO4. 2H2O. It has shown numerous therapeutic effects as a source for calcium. Gypsum may be used to increase hard-tissue healing after injury or surgery by being administered as an oral supplement or directly at the site of injury. Additionally, gypsum has been shown to provide increased water retention and protein stability when used with protein supplements.

Quartz is a very hard mineral composed of silica, SiO2, found worldwide in many different types of rocks, including sandstone and granite. Quartz has been used both inside and outside the body throughout history to promote health and well-being. Quartz crystal is thought to radiate or transmit energy in its crystalline structure. When ingested, the silica-based crystal also may have conductivity characteristics shown by the other silicates in the composition.

Feldspar is silicate of alumina that is composed of potassium and aluminum silicate. Silicates have been shown to possess therapeutic conductive and crystalline properties.

Jarosite is an ocher-yellow mineral occurring on minute rhombohedral crystals that is composed of a hydrous sulphate of iron and potassium. Jarosite has been found to form crystalline lattice structures that increase biomass retention.

Kaolinite is a mineral composed of aluminum silicate. It is often used in pelo-therapy in addition with other clay minerals such as those found in the composition of the present invention. Pelo-therapy is the application of thermal muds for recovering from osteoarthritis and traumatic muscle-bone damages. Kaolinite shows high cation exchange capacity creating the opportunity for both functional and durable medicaments. This mineral is also an aluminum silicate and shares many of the same electrical properties as other silicates used in the composition.

Zeolite is a hydrous silicate of alumina that contains sodium, calcium and aluminum silicate. Sodium zeolite has been shown to increase plasma silicon concentrations and alter bone resorption in animals. More specifically, zeolite has been found to inhibit osteoclast-mediated resorption of bone tissue. Other studies have shown that zeolite increases proliferation, differentiation, and transforming growth factor beta production in normal adult human osteoblast-like cells in vitro. Zeolite shares the aluminum silicate group common to several of the minerals in the composition of the present invention which may lead to therapeutic electrical properties and increase water absorption in joint tissue.

The composition has been shown to alleviate the symptoms of osteoarthritis by decreasing cartilage degradation through glucosaminoglycan release as mediated by IL-1β. Additionally, the composition in combination with other additives has been shown to reduce nitric oxide production in connective tissue. Nitric oxide production by inflammatory cells is known to promote tissue damage in chronic inflammation.

In the preferred embodiment of the invention, the composition is a purified mineral composition comprising: Smectite, Gypsum, Quartz, Feldspar, Jarosite, Kaolinite and Zeolite. In a further preferred embodiment of the invention, the composition includes these minerals in the following ratios Smectite 25-75%, Gypsum 0-20%, Quartz 0-20%, Feldspar 0-20%, Jarosite 0-20%, Kaolinite 0-10% and Zeolite 0-10%. In the most preferred embodiment, the composition includes the above-listed minerals in the following ratios: Smectite about 50%, Gypsum about 10%; Quartz about 10%, Feldspar about 10%, Jarosite about 10%, Kaolinite about 5% and Zeolite about 5%. In a preferred embodiment of the invention, the mineral composition is obtained from natural sources such as rivers, streams or other sources of sedimentary rock. However, the composition may be found in any other natural rock source or may be formulated using synthetic means from a variety of mineral sources. In the most preferred embodiment of the invention, the composition is a purified form of sedimentary silt obtained from a river source.

The composition may also be processed and purified by a number of procedures before being administered to a subject. In a preferred embodiment of the invention, the composition is screened, crushed and heated before being sold for use. Other cleaning steps may also be used to purify the composition. Additionally, the composition may be further processed into particular types of dosage or delivery vehicles.

The present invention also includes a method of treating osteoarthritis by administering a mineral composition to a subject suffering from osteoarthritis. In a preferred embodiment of the invention, the method includes administering a composition containing Smectite, Gypsum, Quartz, Feldspar, Jarosite, Kaolinite and Zeolite. In a preferred embodiment of the invention, the method includes administering the composition containing the minerals in the following ratios: Smectite 25-75%, Gypsum 0-20%, Quartz 0-20%, Feldspar 0-20%, Jarosite 0-20%, Kaolinite 0-10% and Zeolite 0-10%. In the most preferred embodiment, the method includes administering a composition containing the above listed minerals in the following ratios: Smectite about 50%, Gypsum about 10%, Quartz about 10%, Feldspar about 10%, Jarosite about 10%, Kaolinite about 5% and Zeolite about 5%. In the preferred embodiment of the invention, the mineral composition is obtained from natural sources such as rivers, streams or other sources of sedimentary rock. However, the composition may be found in any other natural rock source or may be formulated using synthetic means from a variety of mineral sources. In the most preferred embodiment of the invention, the composition is a purified form of sedimentary silt obtained from a river source.

The method also includes administering the composition to treat inflammatory disease generally. This may include other forms of joint stiffness and joint inflammation that are not directly linked to osteoarthritis. The composition has also shown positive effects in reversing declining bone density, increasing patient energy, improving patient balance and general muscle or joint pain relief.

There are several methods and vehicles for administering the composition to a subject that are within the scope of the method for treating osteoarthritis. These methods include any therapeutically acceptable manner of administering a nutritional supplement or pharmaceutical. In a preferred embodiment of the invention, the mineral composition may be administered as a tablet, capsule, pill, powder, suppository, liquid, drink, intravenous or percutaneous injection, and/or topical cream, gel, ointment, emulsion and/or paste. In these forms, the method of administering the composition may include orally ingesting, injecting, topically applying or administering as a suppository. In a more preferred embodiment of the invention, the method of treating includes administering a tablet, capsule, pill, liquid, powder, or powder mixed with a liquid by oral ingestion.

The composition may also be combined with other additives, inactive or active ingredients to further alleviate the effects of osteoarthritis. Additional active ingredients may include, but are not limited to, pharmaceutical additives such as anti-inflammatories, aspirin, ibuprofen, acetaminophen, naproxen and other additives known for their anti-arthritic or analgesic effects. Other additives may include nutraceutical additives, herbal extracts or other natural ingredients that provide anti-inflammatory, anti-arthritic and analgesic effects. A preferred embodiment of the invention includes a combination of the composition with an herbal extract of *Uncaria guianesis*.

The present method may also include a dosage regimen for administering the above-described composition. The method may include administering the composition on its own or as a supplement to a meal. Additionally, the method may include administering the composition once a day or multiple times a day in order to meet the required dosage. The amount and frequency of the dosage may be further dependent on the physical and health characteristics of the subject. In a preferred embodiment of the invention, the method requires the administration of a single dose to provide the subject with the total required daily amount of mineral composition.

The total dosage amount may also vary according to type and severity of disease. The dosage may also vary depending on the age and health of the subject. A preferred total dosage of the composition is 1.0-100.0 grams per day. The most preferred total dosage is about 2.0 grams per day.

Alternatively, the composition may be directly administered at the site of inflammation or affected tissue through percutaneous injection or transdermal delivery. In a preferred dosage through percutaneous delivery, the composition is extracted through an acid treatment and neutralized before being applied to the inflamed tissue. The preferred dosage through percutaneous delivery may range from 0.001 grams to 10 grams per day.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A dosage form for the treatment of osteoarthritis, consisting essentially of a purified mineral composition and optional excipients, said purified mineral composition consisting essentially of:
   a. 25-75% Smectite;
   b. Gypsum;
   c. Quartz;
   d. Feldspar;
   e. Jarosite;
   f. Kaolinite;
   g. Zeolite; and
   h. an anti-inflammatory selected from the group consisting of aspirin, ibuprofen, acetaminophen, naproxen and mixtures thereof;
      wherein said dosage form is a tablet, capsule, or pill.

2. A method for treating osteoarthritis comprising; administering the composition of claim 1 to a subject suffering from osteoarthritis.

3. A method for treating osteoarthritis comprising: administering a composition to a subject suffering from osteoarthritis; said composition consisting essentially of 25-75% Smectite; Gypsum; Quartz; Feldspar; Jarosite; Kaolinite; Zeolite; optional excipients, and an anti-inflammatory selected from the group consisting of aspirin, ibuprofen, acetaminophen, naproxen and mixtures thereof.

4. The method of claim 3, wherein the composition is in the form of a tablet, powder or capsule.

5. The method of claim 3, wherein the composition is in the form of a tablet or powder.

6. The method of claim 3, wherein the composition is in the form of a capsule.

7. The method of claim 3, wherein the composition is administered percutaneously.

8. The method of claim 3, wherein the subject is human.

9. The method of claim 3, wherein 1.0-100.0 grams of said composition are administered per day.

10. The method of claim 9, wherein 2.0 grams of said composition are administered per day.

* * * * *